US009389208B2

(12) United States Patent
Bailey et al.

(10) Patent No.: US 9,389,208 B2
(45) Date of Patent: Jul. 12, 2016

(54) HERMETIC MANIFOLD FOR ANALYTICAL INSTRUMENTS

(71) Applicant: Rosemount Analytical Inc., Houston, TX (US)

(72) Inventors: Edward J. Bailey, Cypress, TX (US); Jason P. Pratt, Cypress, TX (US); Shane Hale, Jersey Village, TX (US); Gregory J. Golden, Houston, TX (US)

(73) Assignee: Rosemount Analytical Inc., Houston, TX (US)

( * ) Notice: Subject to any disclaimer, the term of this patent is extended or adjusted under 35 U.S.C. 154(b) by 537 days.

(21) Appl. No.: 13/826,774

(22) Filed: Mar. 14, 2013

(65) Prior Publication Data
US 2014/0208827 A1    Jul. 31, 2014

Related U.S. Application Data

(60) Provisional application No. 61/756,653, filed on Jan. 25, 2013.

(51) Int. Cl.
*G01N 30/38* (2006.01)
*G01N 30/32* (2006.01)
*G01N 30/88* (2006.01)
G01N 30/02 (2006.01)
B01D 53/02 (2006.01)

(52) U.S. Cl.
CPC ............. *G01N 30/38* (2013.01); *G01N 30/32* (2013.01); *G01N 30/88* (2013.01); *B01D 53/025* (2013.01); *G01N 2030/025* (2013.01); *G01N 2030/385* (2013.01); *G01N 2030/8881* (2013.01); *Y10T 137/85938* (2015.04)

(58) Field of Classification Search
USPC ........................................................ 73/23.42
See application file for complete search history.

(56) References Cited

U.S. PATENT DOCUMENTS

| 4,068,528 A | * | 1/1978 | Gundelfinger ......... G01N 30/20 73/864.84 |
| 4,471,647 A | | 9/1984 | Jerman et al. |
| 4,474,889 A | | 10/1984 | Terry et al. |
| 4,935,040 A | | 6/1990 | Goedert |
| 5,147,606 A | * | 9/1992 | Charlton ........... B01L 3/502753 422/412 |
| 5,207,109 A | * | 5/1993 | Olsen ..................... G01N 30/20 73/863.73 |

(Continued)

FOREIGN PATENT DOCUMENTS

CN    1756876    4/2006

OTHER PUBLICATIONS

First Office Action for counterpart Chinese Patent Application No. 201410010141.1, from Feb. 28, 2015. English Translation, 18 pages.

(Continued)

*Primary Examiner* — Hezron E Williams
*Assistant Examiner* — Mark A Shabman
(74) *Attorney, Agent, or Firm* — Christopher R. Christenson; Kelly, Holt & Christenson PLLC (57) ABSTRACT

A planar manifold includes a first, generally planar, layer having a plurality of apertures therethrough. A second layer has a plurality of apertures therethrough. A channel layer defines a plurality of channels therein and is interposed between the first layer and the second layer. At least one channel extends in a direction parallel to a plane of the planar manifold and couples an aperture of the first layer to an aperture of the second layer.

13 Claims, 6 Drawing Sheets

(56) References Cited

U.S. PATENT DOCUMENTS

| | | | |
|---|---|---|---|
| 5,340,543 A | 8/1994 | Annino et al. | |
| 5,567,868 A | 10/1996 | Craig et al. | |
| 5,640,995 A * | 6/1997 | Packard | F15C 5/00 137/597 |
| 5,686,657 A | 11/1997 | Craig et al. | |
| 5,808,179 A | 9/1998 | Sittler et al. | |
| 5,997,708 A | 12/1999 | Craig | |
| 6,374,860 B2 | 4/2002 | Xu et al. | |
| 6,612,153 B2 | 9/2003 | White et al. | |
| 1,756,876 A1 | 6/2005 | Harris et al. | |
| 2002/0178786 A1 | 12/2002 | White et al. | |
| 2004/0164265 A1 * | 8/2004 | Killeen | F15C 5/00 251/206 |
| 2005/0098962 A1 * | 5/2005 | Duclos | B29C 70/74 277/628 |

OTHER PUBLICATIONS

Search Report and Written Opinion from corresponding PCT application No. PCT/US2013/071544, dated Mar. 10, 2014, 11 pages.
2nd Office Action from Nov. 9, 2015 for Chinese patent application No. 201410010141.1 11 pages with English translation.

* cited by examiner

HERMETIC MANIFOLD FOR ANALYTICAL INSTRUMENTS

CROSS-REFERENCE TO RELATED APPLICATION

The present application is based on and claims the benefit of U.S. provisional patent application Ser. No. 61/756,653, filed Jan. 25, 2013, the content of which is hereby incorporated by reference in its entirety.

BACKGROUND

Analytical instruments are used in a number of applications to quantitatively and/or qualitatively analyze a sample of interest. Analytical instruments are often found in laboratories and are sometimes employed within processing operations. As used herein, an analytical instrument is any device, system or arrangement that is able to receive a sample of interest and provide an indication of some aspect of the sample of interest. Analytical instruments include, without limitation, process gas analyzers, NO/NOx analyzers, hydrocarbon analyzers, continuous emission monitoring systems and process gas chromatographs.

A variety of analytical instruments employ regulated flows and a variety of flow paths in order to provide analyses regarding various chemicals in processing or analytical contexts. The analytical instruments typically function using one or more flow devices that can initiate, interrupt, and reverse flow through the device. Such variety of flow functions is usually provided by a combination of one or more flow valves and/or pumps. In order to function effectively, analytical instruments will generally include a plurality of sample flow paths. In the context of a gas chromatograph, there are a number of flow paths used to introduce a flow of sample and carrier gas into the analytical instrument; flow a controlled amount of sample across a sorbent column; reverse the flow to elute the sample from the column; and detect the various components in the flow stream. Given the precise nature of such analytical instruments, it is very important that the flow paths themselves do not participate or otherwise affect the chemical make-up of the sample/carrier gas flow.

Typically, the variety of pneumatic or fluid connections of known process analytical instruments requires a variety of discrete tubing connections. While some advances have been provided to include compact planar manifold arrangements consisting of layered passages and gaskets or seals that replace the tubing, such efforts more closely resemble or emulate the planar manifolds of automotive transmission valve bodies and machine tool applications. For example, see U.S. Pat. No. 5,567,868 to Craig. Unfortunately, efforts to date have not resulted in a sufficiently low-cost or chemically-inert manifold.

As the art of process analytic devices has progressed, there is increasing pressure to provide a lower-cost higher-performance device.

SUMMARY

A planar manifold includes a first, generally planar, layer having a plurality of apertures therethrough. A second layer has a plurality of apertures therethrough. A channel layer defines a plurality of channels therein and is interposed between the first layer and the second layer. At least one channel extends in a direction parallel to a plane of the planar manifold and couples an aperture of the first layer to an aperture of the second layer. This functionality can be extended by providing additional layers to the manifold to achieve whatever complexity is required.

DETAILED DESCRIPTION OF ILLUSTRATIVE EMBODIMENTS

Embodiments of the present invention generally improve upon prior manifold attempts by providing an all-polyimide, bonded, multi-layer planar manifold assembly. One suitable, commercially-available polyimide is sold under the trade designation Kapton® available from E. I. du Pont de Nemours and Company of Wilmington, Del. Polyimide is sufficiently inert from most chromatographic applications; is highly dimensionally stable; and is extremely easy to process. Polyimide is commonly used in many circuit boards and flexible circuits. Accordingly, the processing of polyimide is extremely robust and highly efficient and more easily able to provide a very low cost device.

Figure 1:
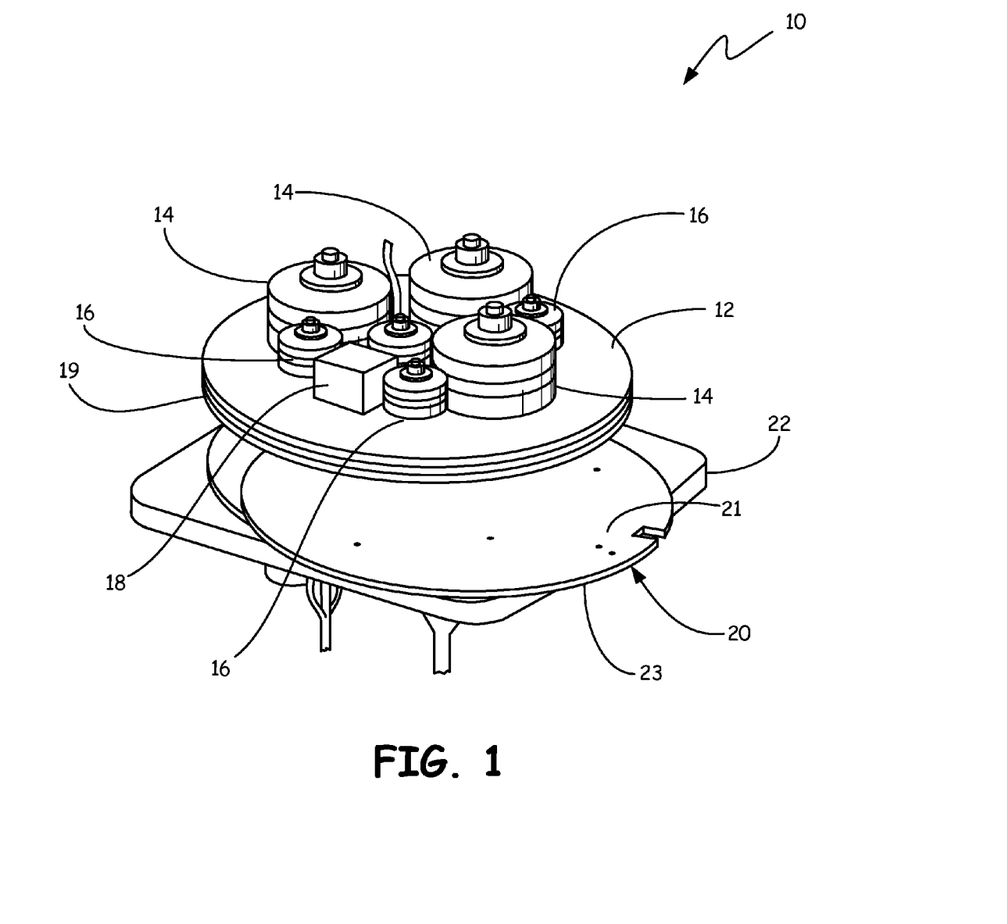
FIG. 1 is a diagrammatic perspective view of a portion of a process gas chromatograph in accordance with an embodiment of the present invention.

FIG. 1 is a diagrammatic perspective view of a portion of a process gas chromatograph 10 in accordance with an embodiment of the present invention. FIG. 1 illustrates a portion of an upper, thermally-controlled portion of process gas chromatograph 10. Specifically, chromatograph 10 includes base plate 12 which is preferably formed of a metal, such as aluminum or stainless steel. A plurality of multi-port flow valves 14 are mounted on base plate 12, along with a plurality of multi-port distribution fittings 16. Additionally, one or more suitable detectors for the process gas chromatograph, such as thermal conductivity detector 18, are also mounted on or proximate base plate 12. One or more chromatographic separation columns (not shown in FIG. 1) are typically mounted proximate the various flow devices within an environmentally-sealed cover. A sample shut-off valve which cuts off flow of sample gas during certain valve actuation configurations may be mounted within proximity of the other flow devices. Within the cover, one or more heaters maintain precise thermal control of the entire assembly. For example, for process gas chromatography, the entire assembly is typically maintained at approximately 80° C. plus or minus a fraction of a degree C.

Base plate 12 includes a plurality of apertures in a lower surface 19 thereof. The apertures pass through base plate 12 and communicate with the various multi-port flow valves 14 and multi-port distribution fittings 16. The apertures in the lower surface 19 of base plate 12 are aligned with corresponding apertures in a first layer 21 of hermetic polyimide manifold 20. Hermetic polyimide manifold 20 is sandwiched between base plate 12 and thermal barrier plate 22. Further, hermetic polyimide manifold 20 includes a number of apertures in both the first layer 21 and an opposing second layer 23 which are aligned with respective apertures in base plate 12 and thermal barrier plate 22 for effective fluidic communication. One or more intermediate channel layers are provided within hermetic polyimide manifold 20 in order to provide arbitrary routing of flow paths therein. Thus, virtually any arrangement of apertures through thermal barrier plate 22 can be routed and/or configured to effectively mate with apertures in lower surface 19 of base plate 12. This ensures that the machining required of thermal barrier plate 22 and base plate 12 is simply drilling straight bores through the plates. The provision of complex flow paths is done exclusively within the one or more channel layers of hermetic polyimide manifold 20.

Figure 2:
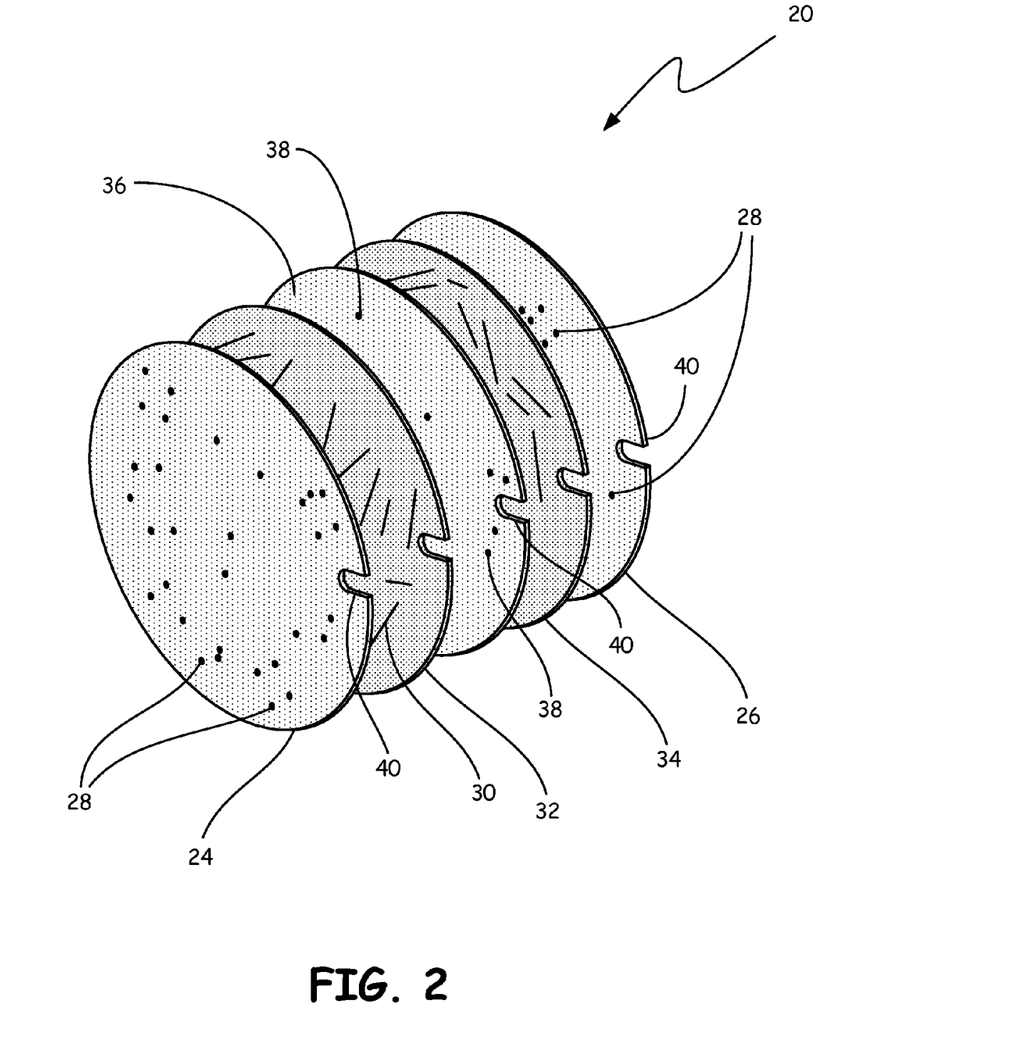
FIG. 2 is an exploded perspective view of a hermetic polyimide manifold in accordance with an embodiment of the present invention.

FIG. 2 is an exploded perspective view of a hermetic polyimide manifold in accordance with an embodiment of the present invention. In the embodiment shown in FIG. 2, a total of five layers are bonded to one another. The manifold 20 consists of two outer layers 24, 26 which include a plurality of apertures 28 therethrough. The apertures 28 of outer layers 24, 26 communicate with various channels 30 in channel layers 32, 34. The channel layers 32, 34 are isolated from one another by an intermediate layer 36 which provides fluidic communication between channel layers 32, 34 via a plurality of apertures 38 therethrough. The various apertures and/or channels can be provided or otherwise created in accordance with any suitable polyimide processing techniques, such as drilling, punching, routing, die-cutting, plasma-etching, et cetera. The resulting structures are highly repeatable and dimensionally stable. Additionally, two or more registration features, such as notch 40, are included such that all of the various apertures are carefully aligned with one another during the lamination or bonding of the various layers 24, 26, 32, 34, and 36 together. Further, the registration features also help to ensure that manifold 20 is carefully aligned with the various apertures in base plate 12 and thermal barrier 22 during assembly.

Figure 3:
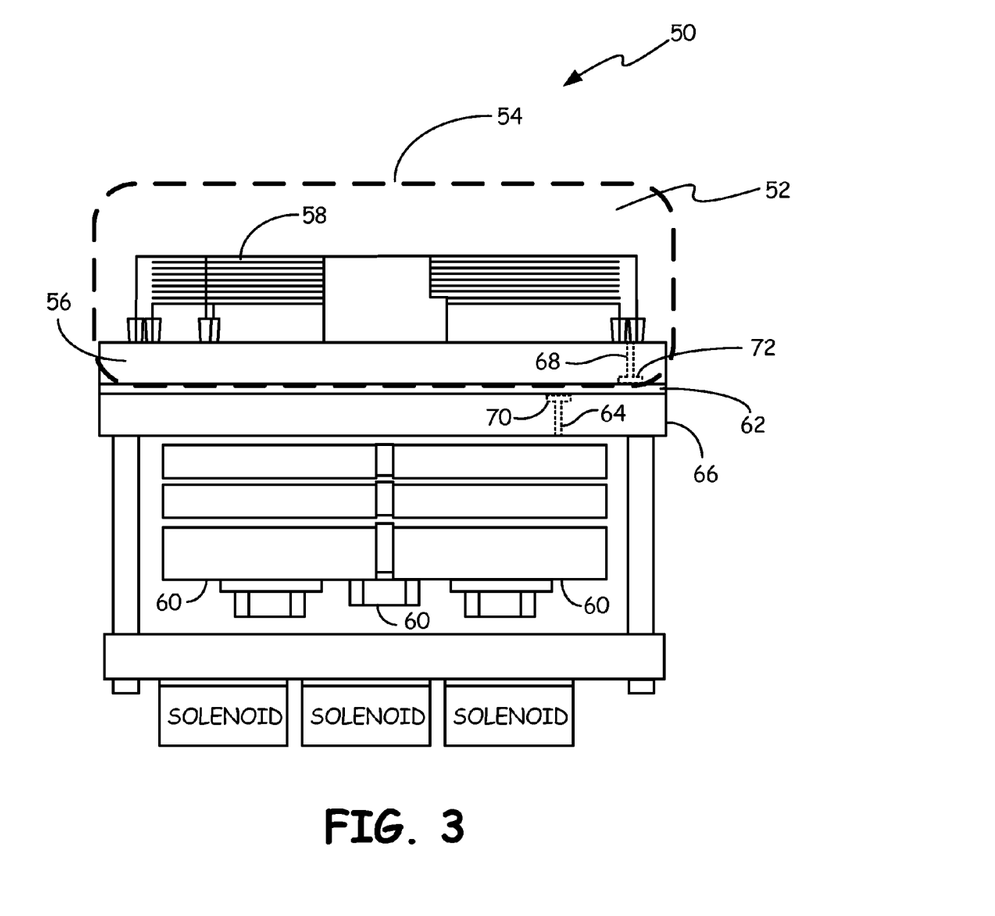
FIG. 3 is a diagrammatic elevation view of a portion of a process gas chromatograph in accordance with another embodiment of the present invention.

FIG. 3 is a diagrammatic elevation view of a portion of a process gas chromatograph in accordance with another embodiment of the present invention. Process gas chromatograph 50 includes a temperature controlled oven 52 defined within cap 54 and plate 56. A number of columns 58 are wound within oven 52 such that gases flowing therein are exposed to the temperature of oven 52. The various columns 58 within oven 52 are coupled to a plurality of multiport selector valves 60 via polyimide manifold 62. The utilization of polyimide manifold 62 allows through hole 64 in plate 66 to be fluidically coupled with through hole 68 in plate 56 even though-holes 64 and 68 are not axially aligned with one another. As indicated in FIG. 3, a seal 70, such as an o-ring, is preferably disposed between plate 66 and polyimide manifold 62 about hole 64 in order to create an airtight connection. Similarly, a seal 72, such as an o-ring, is preferably disposed between plate 56 and polyimide manifold 64 in order to create a second airtight connection. In this manner, any suitable number of arbitrary, airtight connections can be made between plate 66 and plate 56 in order to provide a compact, low-cost structure. Seals 70, 72 may take the form of elastomeric o-rings disposed within annular rings or grooves in their respective plates. Additionally, or alternatively, such seals may be disposed directly on polyimide manifold in any suitable manner, such as screen-printing. Further, while embodiments thus far have only described various fluidic connections that may be made through the polyimide manifold, it is expressly contemplated that any suitable number of electrical connections may also be made therethrough using known printed and/or flex circuit design and manufacturing processes.

Figure 4A:
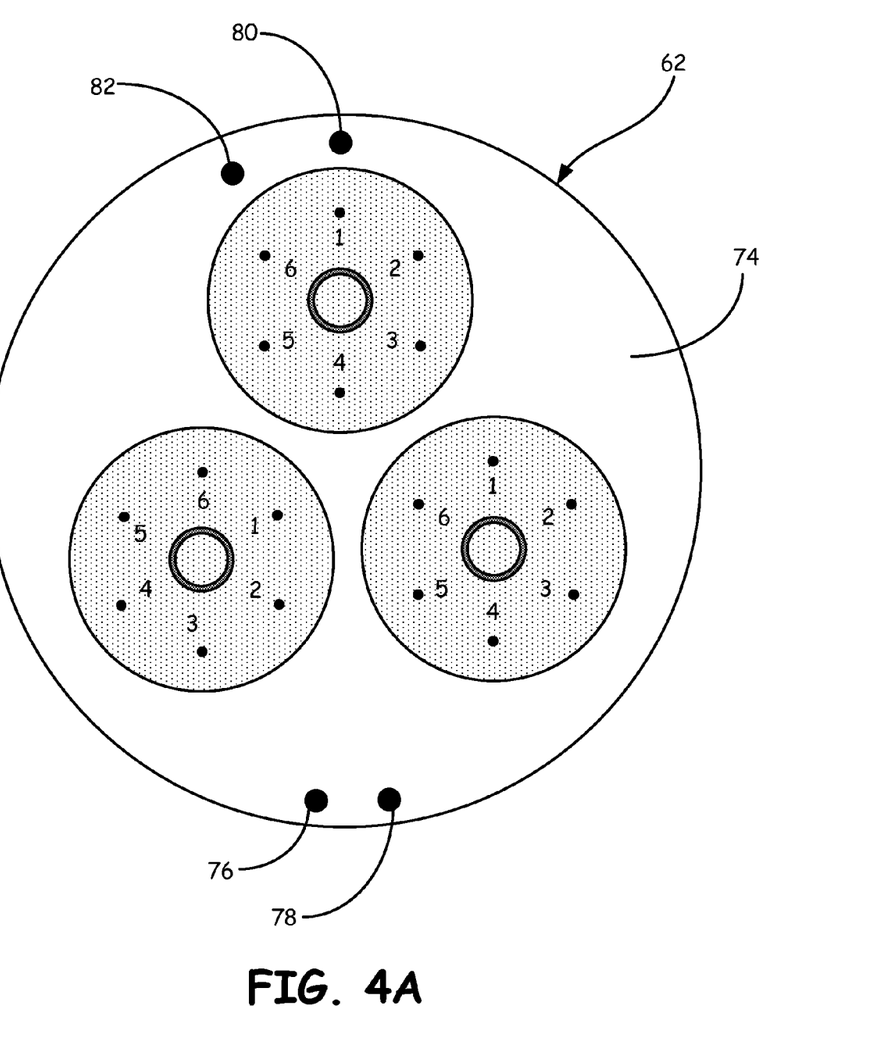
FIGS. 4A and 4B are bottom and top plan views, respectively, of a hermetic polyimide manifold in accordance with an embodiment of the present invention.
Figure 4B:
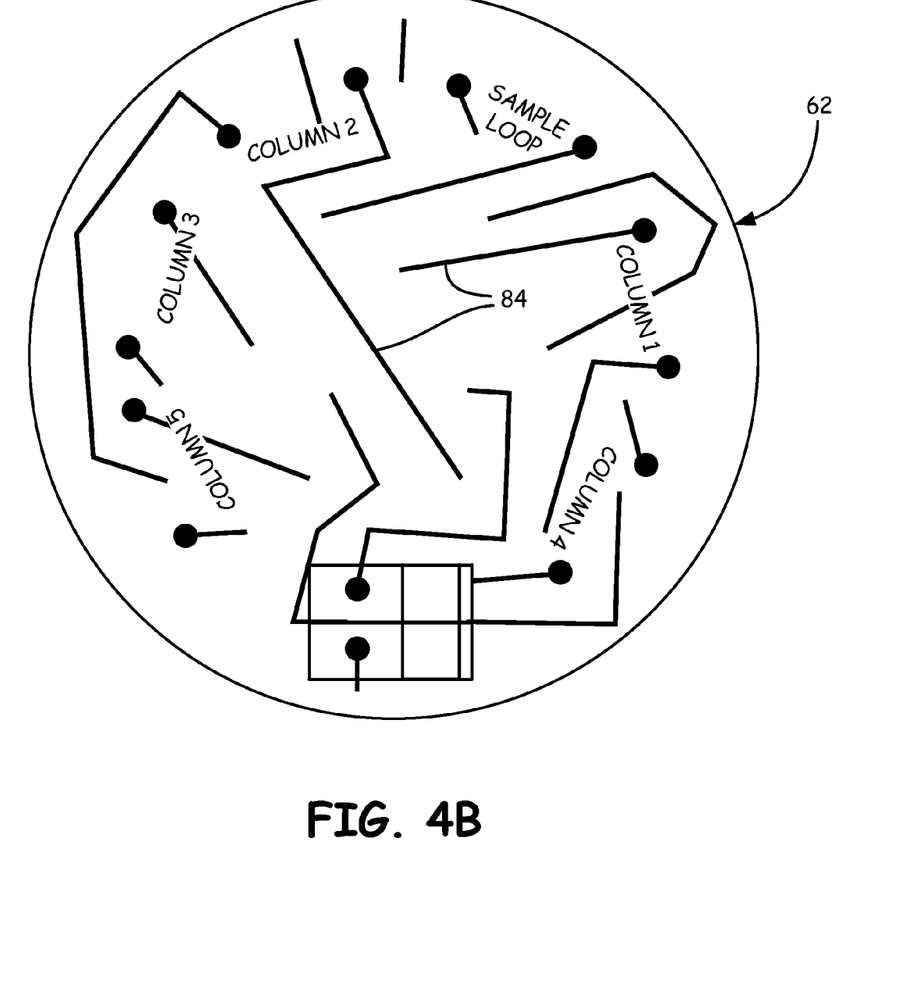

FIGS. 4A and 4B are plan views of bottom and top plates, respectively, of a hermetic polyimide manifold in accordance with an embodiment of the present invention. In the embodiment shown, bottom surface 74 of polyimide manifold 62 includes three sets of apertures (each numbered 1-6) that align with ports of respective multiport selector valves 60 (shown in FIG. 3). Additionally, fluidic connections are also provided for Carrier Gas In (76), Vent (78), Sample In (80), and Sample Out (82). FIG. 4B is a top plan view of manifold 62 with the top layer (comprising apertures aligned with the various column fittings) removed in order to show channel routing. As illustrated, a plurality of non-overlapping channels 84 extend from apertures in bottom surface 74 (shown in FIG. 4A) to coupling locations for various columns and detectors. The various channels 84 generally extend along the plane of the manifold.

Figure 5:
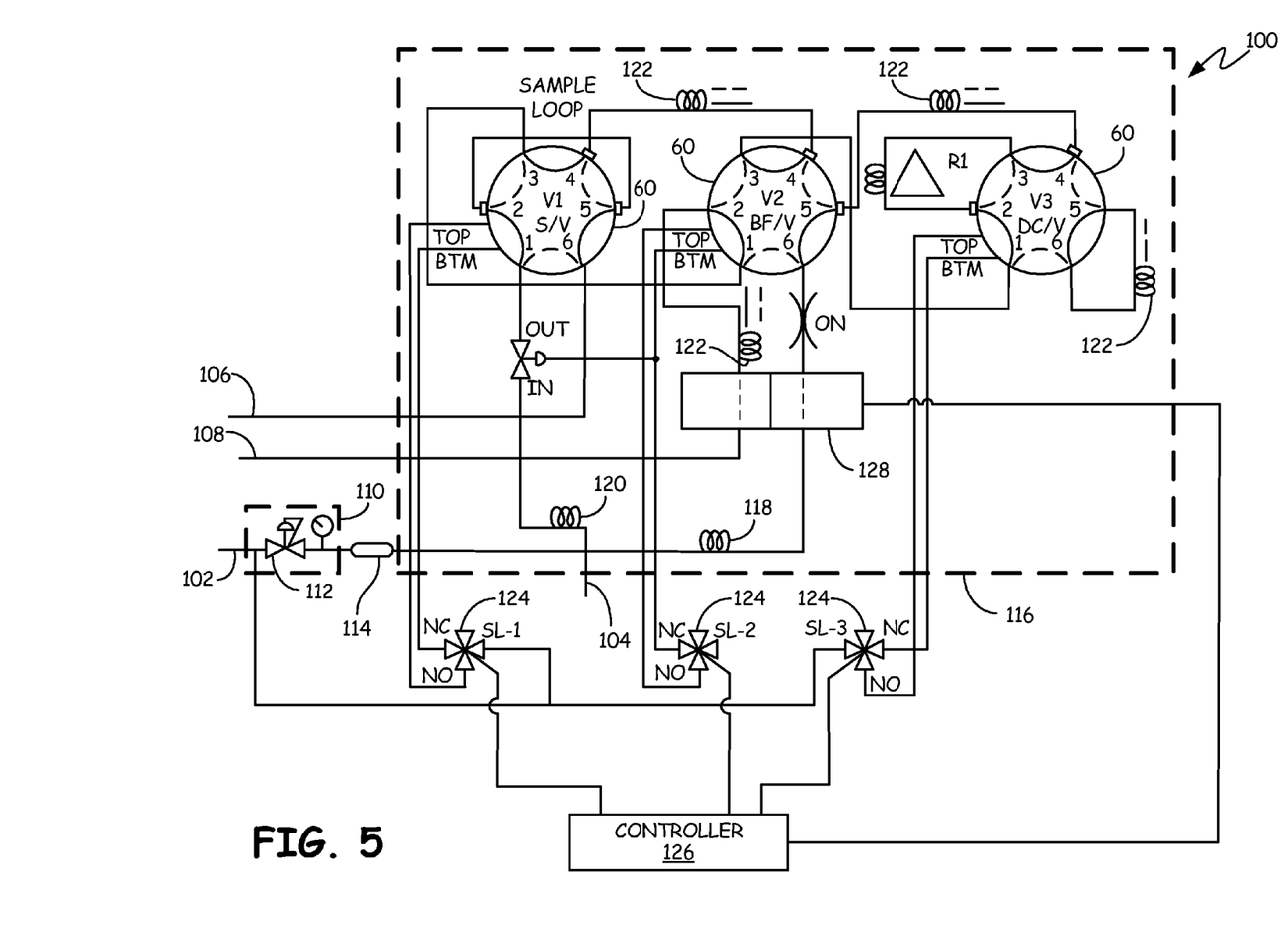
FIG. 5 is a diagrammatic system view of a process gas chromatograph with which embodiments of the present invention are particularly useful.

FIG. 5 is a diagrammatic system view of a process gas chromatograph with which embodiments of the present invention are particularly useful. Process gas chromatograph 100 includes a carrier inlet 102, sample inlet 104, sample vent outlet 106 and measure vent outlet 108 for connecting to suitable sources of carrier gas, sample gas, and appropriate disposal lines. Carrier gas is provided to flow panel 110 where it passes through a regulator 112 and dryer 114 before entering analyzer oven 116 and passing through carrier gas pre-heater coil 118. Sample gas enters chromatograph 100 via sample inlet 104 and passes through sample gas pre-heater coil 120 within analyzer oven 116. Both sample gas and carrier gas eventually enter a plurality of pneumatically-controlled multiport selector valves 60 in order to selectably flow various volumes of sample and/or carrier gas through various chromatographic columns 122 in accordance with known gas chromatography techniques. Each of pneumatically-controlled multiport selector valves 60 is fluidically coupled to a respective solenoid 124 that receives its control signal from controller 126. As shown in FIG. 5, each pneumatically-controlled multiport selector valve 60 has a pair of states. In the first state, the fluidic connections of each valve 60 are shown in solid lines. The fluidic connections of each valve 60 in the second state are shown in phantom. Controller 126 is also operably coupled to detector 128, which is preferably a thermal conductivity detector disposed within analyzer oven 116. Thus, controller 126 is able to fully control flow through gas chromatograph 100 by virtue of controlling solenoids 124. Additionally, controller 126 is able to determine the response of detector 128 to gas flow therethrough. In this way, controller 126 is able to selectably introduce the sample into a chromatographic column for a selected amount of time; reverse the flow of gas through the chromatographic column; and direct the reversed flow through the detector to observe and/or record the detector response over time. This provides chromatographic analysis relative to the sample.

Those skilled in the art will recognize that the embodiment illustrated with respect to FIG. 5 includes no less than 4 distinct columns being operably coupled among three pneumatically-controlled multiport selector valves. Thus, fluidically, the arrangement is quite complex. Employing traditional discrete tubing and associated connections would result in an unmanageable jumble of such tubing and connections. Moreover, the assembly time for simply connecting the various tubes would be significant. Further, each individual tube connection would be subject to the variability of the assembler's torque applied as the fitting is tightened. Further still, each bend or modification that the assembler would be required to introduce in the tubing during assembly could result in damage to the tubing or at least additional variability. However, employing a polyimide manifold in accordance with embodiments of the present invention allows the entire assembly to be more easily constructed in a compact form to produce extremely repeatable connections.

Polyimide manifolds in accordance with embodiments of the present invention can be constructed in any suitable manner. One method of constructing manifold 20 or 62 utilizes multi-layer bonding of polyimide film such as Kapton®. Products based on adhesiveless bonding of polyimide include DuPont's Cirlex®, http://www.cirlex.com/ manufactured by Fralock Corporation of Valencia, Calif. The Fralock process to manufacture Cirlex® sheet products is extended to construct a multi-layer manifold. Cirlex® is an all-polyimide sheet material that can be bonded to itself without using any adhesive. This is advantageous since some laminates may be unreliable at temperatures that exceed the glass transition temperature of the adhesives used in the laminate. Moreover, in process analytic applications where the manifold must not participate in any chemical interaction with the sample, the use of an adhesive can introduce undesirable variability. A second method of constructing a multi-layer manifold includes employing a polyimide printed circuit board sheet material machined to provide the various flowed grooves. The sheet material is then laminated using a conventional screen-printed circuit board adhesive. Other methods of bonding one or more layers of polyimide together can be provided in accordance with embodiments of the present invention. Further still, the multi-layer manifold could be bonded directly to one or more metallic or polymeric outer layers to eliminate the need for seals between the metal housing and the manifold. Additionally, given that at least some embodiments of the present invention employ processing techniques that are more commonly found in printed circuit board manufacturing, such embodiments can include having one or more elastomeric seals screen-printed proximate apertures on the outer surfaces of the manifold assembly such that when the assembly is sandwiched between thermal barrier layer 22 and base plate 12, no additional O-rings or other elastomeric sealing structures are required. Additionally, while the fluidic manifold has been described as being of polyimide material, other materials including printed circuit board materials (glass epoxies et cetera), plastics, and metals along with various bonding techniques may be employed to achieve the construction of a manifold in accordance with embodiments of the present invention.

Given the context of printed circuit board processing, the various channels of manifolds in accordance with embodiments of the present invention can be designed with standard printed circuit board design software, where the channels are designed instead of circuit traces. Such tools include advanced features such as impedance matching and/or advanced routing algorithms. These techniques can be extended to provide channels having identical length or volume flow paths within the manifold assembly. This may ensure that a sample gas, carrier gas or other gases flowing through the manifold are subjected to the manifold environment for exactly the same amount of time as one another.

Embodiments of the present invention, as set forth above, can provide a low-cost, robust manifold assembly that is extremely dimensionally stable and chemically inert. Moreover, it is believed that employing the hermetic polyimide manifold set forth in accordance with embodiments of the present invention, can result in a higher-performance, lower cost structure which can therefore, increase performance and reduce the cost of the overall process analytic device in which it is employed. Further still, given the extreme repeatability and stability of polyimide, it is believed that should a failure or repair be required with respect to a manifold, a new manifold simply be inserted in place for a defective or non-functioning manifold without needing to recalibrate the entire process analytic device.

Although the present invention has been described with reference to preferred embodiments, workers skilled in the art will recognize that changes may be made in form and detail without departing from the spirit and scope of the invention. For example, while embodiments of the present invention have been described with respect to a process gas chromatograph, it is expressly contemplated that embodiments of the present invention are practicable in any context where a significant number of fluidic connections must be made, and where the material through which the fluid flows must not chemically alter or otherwise influence the fluid.

What is claimed is:

1. A planar manifold comprising:
   a first layer having a first plurality of apertures therethrough, the first plurality of apertures being aligned with a plurality of corresponding column fittings, the first layer being generally planar;
   a second layer having a second plurality of apertures therethrough, the second plurality of apertures being aligned with a plurality of corresponding selector valve ports;
   a channel layer defining a plurality of channels therein, the channel layer being interposed between the first layer and the second layer, wherein at least one channel extends in a direction parallel to a plane of the planar manifold and couples an aperture of the first layer to an aperture of the second layer; and
   wherein the planar manifold is hermetically sealed and constructed from polyimide.

2. The planar manifold of claim 1, wherein the first layer, second layer, and channel layer are laminated together.

3. The planar manifold of claim 2, wherein the entire planar manifold is constructed from adhesive-less polyimide.

4. The planar manifold of claim 1, and further comprising:
   a third layer having a third plurality of apertures therethrough; and
   a second channel layer defining a second plurality of channels and being interposed between the second and third layers, wherein at least one channel of the second plurality of channels extends in a direction parallel to a plane of the planar manifold and couples an aperture of the second layer to an aperture of the third.

5. The planar manifold of claim 4, wherein the first layer, second layer, third layer and both channel layers are laminated together.

6. The planar manifold of claim 5, wherein the entire planar manifold is constructed from adhesive-less polyimide.

7. The planar manifold of claim 4, and further comprising:
   a fourth layer having a fourth plurality of apertures therethrough; and
   a third channel layer defining a third plurality of channels and being interposed between the third and fourth layers, wherein at least one channel of the third plurality of channels extends in a direction parallel to a plane of the planar manifold and couples an aperture of the third layer to an aperture of the fourth layer.

8. The planar manifold of claim 1, and further comprising an elastomeric ring disposed about at least one of the apertures of the first layer.

9. The planar manifold of claim 8, wherein the elastomeric ring is screen-printed on the first layer.

10. The planar manifold of claim 1, and further comprising at least one conductor providing an electrical connection between the first layer and the second layer.

11. The planar manifold of claim 1, and further comprising a plurality of alignment features extending through the first, second and channel layers.

12. The planar manifold of claim 11, wherein the alignment features are holes.

13. The planar manifold of claim 11, wherein at least one alignment feature is a notch disposed at a periphery of the planar manifold.

* * * * *